United States Patent
Takakura et al.

(10) Patent No.: US 8,182,795 B2
(45) Date of Patent: May 22, 2012

(54) OIL-IN-WATER EMULSION TYPE SUNSCREEN PREPARATION

(75) Inventors: Yoshihito Takakura, Yokohama (JP); Kazuaki Suzuki, Yokohama (JP); Takayuki Omura, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 223 days.

(21) Appl. No.: 12/670,744

(22) PCT Filed: Jul. 27, 2007

(86) PCT No.: PCT/JP2007/000801
§ 371 (c)(1),
(2), (4) Date: Jan. 26, 2010

(87) PCT Pub. No.: WO2007/122822
PCT Pub. Date: Nov. 1, 2007

(65) Prior Publication Data
US 2010/0209365 A1 Aug. 19, 2010

(51) Int. Cl.
- A61K 8/06 (2006.01)
- A61K 31/53 (2006.01)
- A61K 31/216 (2006.01)
- A61K 31/277 (2006.01)
- A61K 31/045 (2006.01)
- A61Q 17/04 (2006.01)

(52) U.S. Cl. ............ 424/60; 424/59; 514/246; 514/506; 514/519; 514/724; 514/937; 514/938; 514/941; 514/942

(58) Field of Classification Search .................. None
See application file for complete search history.

(56) References Cited

U.S. PATENT DOCUMENTS

| | | | |
|---|---|---|---|
| 5,723,482 A * | 3/1998 | Degwert et al. | 514/399 |
| 5,851,517 A | 12/1998 | Mougin | |
| 6,395,262 B1 | 5/2002 | Favre | |
| 6,699,460 B2 * | 3/2004 | Candau | 424/59 |
| 2002/0136746 A1 * | 9/2002 | Klug et al. | 424/401 |
| 2004/0151793 A1 * | 8/2004 | Paspaleeva-kuhn et al. | 424/754 |

FOREIGN PATENT DOCUMENTS

| | | |
|---|---|---|
| EP | 0691126 A1 | 6/1995 |
| JP | 08-026972 A | 1/1996 |
| JP | 10-101521 A | 4/1998 |
| JP | 2005-32063 A | 11/2005 |
| WO | 97/00663 A1 | 1/1997 |
| WO | 03/053391 A1 | 7/2003 |

OTHER PUBLICATIONS

Drugfuture ([online] downloaded on Oct. 28, 2011 from: http://www.drugfuture.com/chemdata/polyoxyethylene-fatty-acid-esters.html on Oct. 28, 2011; 1 page).*

* cited by examiner

*Primary Examiner* — Ernst Arnold
(74) *Attorney, Agent, or Firm* — Townsend & Banta

(57) ABSTRACT

An oil-in-water emulsified sunscreen cosmetic which contains:
(A) Containing the following three types of surfactants (A-1)-(A-3);
   (A-1) A POE stearic ester having a POE mole number of 20-120;
   (A-2) sorbitan tristearate; and
   (A-3) glyceryl stearate having a HLB of 5-8;
(B) bis-ethylhexyloxyphenolmethoxyphenyltriazine and/or tert-butylmethoxybenzoylmethane, oil soluble ultraviolet absorbents, solid at room temperatures;
(C) ethylhexyl methoxycinnamate and/or octocrylene, oil soluble ultraviolet absorbents, liquid at room temperature;
(D) phenylbenzimidazolesulfonic acid, a water soluble ultraviolet absorbent; and
(E) a higher alcohol having 14-24 carbon atoms.

4 Claims, No Drawings

OIL-IN-WATER EMULSION TYPE SUNSCREEN PREPARATION

"This application is a 371 (PCT national stage) application of corresponding PCT application No. PCT/JP2007/000801 filed Jul. 27, 2007."

TECHNICAL FIELD

The present invention relates to a sunscreen cosmetic. More specifically, it relates to an oil-in-water emulsified sunscreen cosmetic that is superior in ultraviolet protection as well as in stability and the sensation during use.

BACKGROUND ART

In the field of sunscreen cosmetics, efforts are being made to improve the sensation during use and stability of the base agent while increasing the ultraviolet protection.

For example, Patent Document 1 discloses an oil-in-water emulsified sunscreen cosmetic comprising (a) a phospholipid, (b) a non-ionic surfactant and/or anionic surfactant, (c) an oil soluble ultraviolet absorbent, (d) water, (e) a microbial polysaccharide, (f) sterin, and (g) a water soluble ultraviolet absorbent, said sunscreen cosmetic having a low viscosity, showing no separation or increased viscosity over time, indicating superior stability, and giving refreshing and moist tactile sensations.

Patent Citation 1: Japanese Patent Laid-Open 2005-255669 bulletin

DISCLOSURE OF INVENTION

Technical Problem

When the ultraviolet absorbent content is increased in order to increase the ultraviolet protection, usability and the stability of the base agent become poor. Therefore, the market has long been desiring to improve usability and the stability of the base agent while increasing the ultraviolet protection at the same time, and this has been a very important issue for those skilled in the art.

The inventors addressed this important issue and conducted earnest research, and, to our surprise, discovered that an oil-in-water emulsified composition having a specific composition including a specific surfactant, ultraviolet absorbent, and other ingredients functions as a sunscreen cosmetic that increases the ultraviolet protection and at the same time improve the sensation during use and the stability of the base agent, thus completing the present invention.

In addition, in the present invention it was also discovered that, even when β-alanyl-L-histidine and/or its salt (trivial name: carnosine) was added, an increase in the pH of the base agent due to carnosine, which was a basic dipeptide, could be prevented.

Technical Solution

That is, the present invention provides a oil-in-water emulsified sunscreen cosmetic that satisfies all of the following conditions (A), (B), (C), (D), and (E):

(A) Containing the following three types of surfactants (A-1)-(A-3) in the amount of 1-6 wt % of the total amount of the cosmetic (A-1) A POE stearic ester having a POE mole number of 20-120

(A-2) Sorbitan tristearate (A-3) Glyceryl stearate having a HLB of 5-8

(B) Containing the following oil soluble ultraviolet absorbent, which is solid at room temperature, in the amount of 0.01-5 wt % of the total amount of the cosmetic Bis-ethylhexyloxyphenolmethoxyphenyltriazine and/or tert-butylmethoxybenzoylmethane (C) Containing the following oil soluble ultraviolet absorbent that is liquid at room temperature, in the amount of 1-14 wt % of the total amount of the cosmetic Ethylhexyl methoxycinnamate and/or octocrylene (D) Containing the following water soluble ultraviolet absorbent in the amount of 0.1-5 wt % of the total amount of the cosmetic Phenylbenzimidazolesulfonic acid or its salt (E) Containing a higher alcohol having 14-24 carbon atoms Also, the present invention provides the aforementioned oil-in-water emulsified sunscreen cosmetic that satisfies the following conditions (1) and (2):

(1) The ingredient (A-3) content is 10-75 wt % of the total amount of ingredients (A-1), (A-2), and (A-3).

(2) The ingredient (E) content is 30-90 wt % of the total amount of ingredients (A-1), (A-2), and (A-3).

Furthermore, the present invention provides the aforementioned oil-in-water emulsified sunscreen cosmetic (F) further containing a monoester oil represented by the following formula (1) in the amount of 0.2-9 wt % of the total amount of the cosmetic.

[Chemical formula 1]

(In this formula, $R_1$ denotes an alkyl group having 5-11 carbon atoms, and $R_2$ denotes an alkyl group having 3-11 carbon atoms.)

Furthermore, the present invention provides the aforementioned oil-in-water emulsified sunscreen cosmetic (G) further containing a random copolymer ether compound of ethylene glycol and propylene glycol represented by the following formula (2) in the amount of 0.2-9 wt % of the total amount of the cosmetic.

[Chemical formula 2]

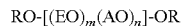

(In this formula, AO denotes an oxyalkylene group having 3-4 carbon atoms, EO denotes an oxyethylene group, m and n, respectively, are average addition mole numbers of said oxyalkylene group and oxyethylene group; also $1 =< m =< 70$ and $1 =< n =< 70$. The ratio of the oxyethylene group to the total of the oxyalkylene group having 3-4 carbon atoms and the oxyethylene group is 50-100 wt %. The oxyalkylene group having 3-4 carbon atoms and the oxyethylene group are randomly added. R denotes a hydrocarbon group having 1-4 atoms or a hydrogen atom, each different or identical, and the ratio of the number of hydrogen atoms to the number of the hydrocarbon groups is 0.15 or less.)

Furthermore, the present invention provides the aforementioned oil-in-water emulsified sunscreen cosmetic (H) further containing β-alanyl-L-histidine and/or its salt in the amount of 0.1-4.5 wt % of the total amount of the cosmetic and the cosmetic's pH being less than 8.

Advantageous Effects

According to the present invention, it is possible to provide a sunscreen cosmetic that improves the ultraviolet protection, stability of the base agent, and the sensation during use.

As a result, in the present invention, even when phenylbenzimidazolesulfonic acid or its salt is added at the high level of 5 wt %, the emulsification stability of the base agent improves, not to mention an increased ultraviolet protection due to the blend ratio.

Also, by selecting a specific surfactant and adding it at a specific composition ratio along with other essential ingredients, the high temperature stability and usability of the prepared oil-in-water emulsified composition are improved.

Furthermore, by adding a specific monoester oil, it is possible to prevent degradation of the appearance of the sunscreen cosmetic due to the temperature cycling.

In addition, in the present invention, even when carnosine is added, it is possible to prevent an increase in the pH of the base agent due to carnosine.

BEST MODE FOR CARRYING OUT THE INVENTION

The configuration of the present invention is described in detail below.

(A) Containing the following three types of surfactants (A-1)-(A-3) in the amount of 1-6 wt % of the total amount of the cosmetic.

(A-1) A POE stearic ester having a POE mole number of 20-120

(A-2) Sorbitan tristearate (A-3) Glyceryl stearate having a HLB of 5-8

Ingredients (A-1)-(A-3) are prior art ingredients of cosmetics and they function as surfactants in the present invention.

Ingredient (A-3), i.e. glyceryl stearate having a HLB of 5-8, is prepared by mixing an arbitrary higher fatty acid with glyceryl stearate to adjust the HLB to 5-8.

These three types of surfactants are added in the amount of 1-6 wt % of the total amount of the cosmetic. If it is less than 1 wt %, then the high temperature stability becomes poor. On the other hand, if it is over 6 wt %, then a sticky sensation becomes noticeable during use. The preferable range is 1.5-5.5 wt %.

<Conditions of (1) of Claim 2>

Particularly, the ingredient (A-3) content is preferably 10-75 wt % of the total amount of ingredients (A-1), (A-2), and (A-3). More preferably, the ingredient (A-3) content is 20-70 wt % of the total amount of ingredients (A-1), (A-2), and (A-3). If it is less than 10 wt %, then the high temperature stability becomes poor. On the other hand, if it is over 75 wt %, then not only the sensation during use (absorption and stickiness) deteriorates but the stability also deteriorates.

(B) Containing the following oil soluble ultraviolet absorbent, which is solid at room temperature, in the amount of 0.01-5 wt % of the total amount of the cosmetic.

Bis-ethylhexyloxyphenolmethoxyphenyltriazine and/or tert-butylmethoxybenzoylmethane In the present invention, there is no risk of the ultraviolet absorbent precipitating as a solid at room temperature even if an oil soluble ultraviolet absorbent that is solid at room temperature is added to improve the ultraviolet protection.

The oil soluble ultraviolet absorbent used in the present invention is bis-ethylhexyloxyphenolmethoxyphenyltriazine and/or tert-butylmethoxybenzoylmethane, which are prior art ultraviolet absorbents.

The blend ratio of the aforementioned ultraviolet absorbent is 0.01-5 wt %, preferably 0.1-4.5 wt %, of the total amount of the cosmetic. If the blend ratio is 0.01 wt % or less, then effective ultraviolet protection cannot be obtained, and if it is 5 wt % or more, then the stability deteriorates (such as precipitation of crystals at low temperatures).

In the present invention, room temperature indicates 25° C.

(C) Containing the following oil soluble ultraviolet absorbent that is liquid at room temperature, in the amount of 1-14 wt % of the total amount of the cosmetic.

Ethylhexyl methoxycinnamate and/or octocrylene

In the present invention, the aforementioned oil soluble ultraviolet absorbent that is liquid at room temperature is added to improve the ultraviolet protection and solubility of said ingredient (B).

The oil soluble ultraviolet absorbent that is liquid at room temperature used in the present invention is ethylhexyl methoxycinnamate and/or octocrylene, which are prior art ultraviolet absorbents.

The blend ratio of the aforementioned ultraviolet absorbent is 1-14 wt %, preferably 3-12 wt %, of the total amount of the cosmetic. When the blend ratio is 1 wt % or less, then solubility of said ingredient (B) deteriorates and therefore the stability deteriorates (such as precipitation of crystals at low temperatures). If the blend ratio is over 14 wt %, then the sensation during use (stickiness) due to this ingredient becomes prominent and the high temperature stability also deteriorates.

(D) Containing the following water soluble ultraviolet absorbent in the amount of 0.1-15 wt % of the total amount of the cosmetic.

Phenylbenzimidazolesulfonic acid or its salt

Furthermore, phenylbenzimidazolesulfonic acid or its salt, as a water soluble ultraviolet absorbent, is added to the present invention. The salt is Na salt, Ka salt, and/or triethanolamine salt.

Phenylbenzimidazolesulfonic acid or its salt is added to further improve the ultraviolet protection. At the same time, it turned out surprisingly that the addition of this ultraviolet absorbent also contributed to an improvement in the stability of the base agent and usability.

The water soluble ultraviolet absorbent is phenylbenzimidazolesulfonic acid or its salt, which are prior art ultraviolet absorbents.

The blend ratio of the aforementioned ultraviolet absorbent is 0.1-5 wt %, preferably 0.5-3 wt %, of the total amount of the cosmetic. This addition is to improve the ultraviolet protection. If the blend ratio is less than 0.1 wt %, then not only the ultraviolet protection cannot be obtained but also sufficient emulsification cannot be obtained and usability (absorption) also deteriorates. If the blend ratio is over 5 wt %, then the sensation during use (stickiness) due to this ingredient becomes prominent.

(E) Containing a higher alcohol having 14-24 carbon atoms.

In the present invention, it was discovered that the addition of a higher alcohol having 14-24 carbon atoms, in addition to the aforementioned essential ingredients, improved the stability of the base agent and usability.

This effect is not guaranteed if the number of carbon atoms is outside of this range. A more preferable number of carbon atoms is 16-22.

Specific examples of preferable higher alcohols include cetanol, stearyl alcohol, and behenyl alcohol.

<Condition (2) of Claim 2>

The blend ratio of the aforementioned higher alcohol {referred to as ingredient (E)} is preferably 30-90 wt %, more preferably 35-85 wt %, of the total amount of ingredients (A-1), (A-2), and (A-3). If it is less than 30 wt %, then the high temperature stability cannot be secured. On the other hand, if it is over 90 wt %, then the stability over temperature cycling deteriorates and poor absorption due to the higher alcohol affects the sensation during use.

<Claim 3>
(F) Containing the monoester oil represented by the following formula (1) in the amount of 0.2-9 wt % of the total amount of the cosmetic.

[Chemical formula 3]

$$R_1COOR_2 \quad (1)$$

(In this formula, $R_1$ denotes an alkyl group having 5-11 carbon atoms, and $R_2$ denotes an alkyl group having 3-11 carbon atoms.)

It is preferable that the aforementioned monoester oil (referred to as ingredient F) is further added to the present invention. The addition of this can prevent deterioration of the appearance due to temperature cycling and also improve the sensation during use (absorption). Preferable ester oils are those whose R1 and R2 are alkyl groups having 9 or less carbon atoms; and more preferable are 2-ethylhexyl 2-ethylhexanoate and isononyl isononoate.

The blend ratio of the aforementioned monoester is 0.2-9 wt %, preferably 0.5-8 wt %, of the total amount of the cosmetic. If the blend ratio is less than 0.2 wt %, then there is not enough effect on usability and stability. On the other hand, if the blend ratio is over 9 wt %, then there is an adverse effect on the high temperature stability.

<Claim 4>
(G) Containing the random copolymer ether compound of ethylene glycol and propylene glycol represented by the following formula (2) in the amount of 0.2-9 wt % of the total amount of the cosmetic.

[Chemical formula 4]

$$RO\text{-}[(EO)_m(AO)_n]\text{-}OR \quad (2)$$

(In this formula, AO denotes an oxyalkylene group having 3-4 carbon atoms, EO denotes an oxyethylene group, m and n, respectively, are average addition mole numbers of said oxyalkylene group and oxyethylene group; also $1=<m=<70$ and $1=<n=<70$. The oxyalkylene group having 3-4 carbon atoms and the oxyethylene group are randomly added. R denotes a hydrocarbon group having 1-4 atoms or a hydrogen atom, each different or identical, and the ratio of the number of hydrogen atoms to the number of the hydrocarbon groups is 0.15 or less.)

It is preferable that the aforementioned random copolymer ether compound (referred to as ingredient G) is further added to the present invention. By adding this, effects such as an improvement in the high temperature stability, in the sensation during use (absorption and stickiness), and also in the emulsification are achieved.

Preferable random copolymer ether compounds are those represented by formula (2) wherein m=14 and n=7, as well as m=17 and n=4.

The blend ratio of the aforementioned random copolymer ether compound is 0.2-9 wt %, preferably 0.5-5 wt %, of the total amount of the cosmetic. If the blend ratio is less than 0.2 wt %, then there is not enough effect on usability, stability, and emulsification. On the other hand, if the blend ratio is over 9 wt %, then there is an adverse effect on the high temperature stability.

(H) Containing β-alanyl-L-histidine and/or its salt (trivial name: carnosine; referred to as ingredient H) in the amount of 0.1-4.5 wt % of the total amount of the cosmetic and the pH of the cosmetic is lower than 8.

The present invention is a sunscreen cosmetic. Condition (H) is a condition for the case where a prior art material carnosine is further added, as an antioxidant and/or anti-wrinkling agent, to the sunscreen cosmetic of the present invention.

That is, the present invention manifests a prominent effect of preventing an increase in the pH of the base agent even when carnosine, which is an basic dipeptide, is added. That is, the increase in the pH of the cosmetic of the sunscreen cosmetic of the present invention can be controlled under 8 even when carnosine is added and therefore this is incorporated as condition (H).

The aforementioned effect is manifested when carnosine, ingredient (H), is added in the amount of 0.1-4.5 wt % of the total amount of the cosmetic. In particular, the pH increase due to this ingredient can be kept under 8 even when the blend ratio is as high as 1-3 wt %, which makes the present invention very significant.

The oil-in-water emulsified sunscreen cosmetic of the present invention is prepared as an oil-in-water emulsified composition by adding water and water soluble cosmetic ingredients, oil ingredients, and powder to the aforementioned essential ingredients, followed by mixing by a conventional method.

The blend ratio of water is 20-80 wt %, preferably 30-60 wt %, of the total amount of the cosmetic.

In addition to the aforementioned essential ingredients, other ingredients used in cosmetics can be blended as necessary in the oil-in-water sunscreen cosmetic of the present invention; examples of such ingredients include powder ingredients, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, ultraviolet absorbents, sequestering agents, lower alcohols, polyhydric alcohols, sugars, amino acids, organic amines, polymer emulsions, pH adjusting agents, skin nutrients, vitamins, antioxidants, antioxidation assistants, perfumes, and water; and the endermic liniment can be prepared for the target formulation with a conventional method. Specific ingredients which can be blended in are listed below. The skin cosmetic of the present invention can be prepared by blending the aforementioned essential ingredients and any one, two or more of the following ingredients.

Examples of the powder ingredients include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, myristic acid zinc, calcium palmitate, and aluminum stearate), and boron nitride); organic powders (for example, polyamide resin powder (nylon powder), polyethylene powder, poly-methyl methacrylate powder, polystyrene powder, powders of the copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and loess); inorganic black pigments (for example, black iron oxide and low oxides of titanium); inorganic purple pigments (for example, manganese violet, cobalt violet); inorganic green pigments (for example, chromium oxide, chromium hydroxide, and cobalt titanate);

inorganic blue pigments (for example, ultramarine blue and Berlin blue); pearl pigment (for example, titania coated mica, titania coated bismuth oxychloride, titania coated talc, coloration titania coated mica, bismuth oxychloride, fish scale flakes); metal powder pigments (for example, aluminium powder, copper powder); organic pigments such as Zr, barium or aluminium rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1; and natural colors (for example, chlorophyll and β-carotene).

Examples of the liquid fats and oils include avocado oil, tsubaki oil, turtle fatty acid, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, *perilla* oil, soybean oil, peanut oil, tea seed oil, Japanese nutmeg oil, rice bran oil, Chinese gimlet oil, Japanese gimlet oil, jojoba oil, germ oil, and triglycerin.

Examples of the solid fats and oils include cacao butter, coconut oil, hydrogenated coconut oil, palm oil, palm kernel oil, Japanese core wax nucleus oil, hydrogenated oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Examples of the hydrocarbon oils include liquid petrolatum, ozocerite, squalane, pristane, paraffin, ceresin, squalene, petrolatum, and microcrystallin wax.

Examples of the higher fatty acids include lauric acid, myristic acid, palmitic acid, stearic acid, behenic acid, oleic acid, undecylenic acid, tall oil fatty acid, isostearic acid, linolic acid, linoleic acid, eicosapentaenoic acid (EPA), and docosahexaenoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain ethyl alcohols (for example, mono stearyl glycerin ether (batyl alcohol), 2-decyltetradecynol, lanolin alcohol, cholesterol, phytosterol, hexyl dodecanol, iso stearyl alcohol, and octyl dodecanol).

Examples of the ester oils include isopropyl myristate, cetyl octanoate, octyl dodecyl myristate, isopropyl palmitate, butyl stearate, hexyl laurate, myristil myristate, decyl oleate, dimethyl hexyl decyl octanoate, cetyl lactate, myristil lactate, lanolin acetate, iso cetyl stearate, iso cetyl isostearate, cholesteryl 12-hydroxystearate, di-2-ethylene glycol ethylhexanoate, dipentaerythritol fatty acid ester, n-alkylene glycol monoisostearate, neopentyl glycol dicaprate, diisostearyl malate, glyceryl di-2-heptylundecanoate, trimethylolpropane tri-2-ethyl hexanoate, trimethylolpropane triisostearate, tetra-2-pentaerythritol ethylhexanoate, glycerin tri2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, methyl castor oil fatty acid, oleyl oleate, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane); ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, and various modified polysiloxanes (amino-modified polysiloxane, polyether-modified polysiloxane, alkyl-modified polysiloxane, and fluorine-modified polysiloxane).

Examples of the anionic surfactants include fatty acid soaps (for example, sodium laurate and sodium palmitate); higher alkyl sulfuric ester salts (for example, sodium lauryl sulfate and potassium laurylsulfate); alkylether sulfuric ester salts (for example, POE-triethanolamine laurylsulfate and sodium POE-lauryl sulfate); N-acyl sarcosinic acids (for example, sodium N-lauroyl sarcosinate); higher fatty acid amide sulfonic acid salts (for example, sodium N-myristoyl N-methyl taurate, sodium cocoyl methyl taurate, and sodium laurylmethyl taurate); phosphoric ester salts (for example, sodium POE-oleyl ether phosphate and POE stearyl ether phosphoric acid); sulfosuccinates (for example sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (for example, sodium linear dodecyl benzene sulfonate, triethanolamine linear dodecyl benzene sulfonate, linear dodecyl benzene sulfonic acid); higher fatty acid ester sulfates (for example, hydrogenated coconut oil aliphatic acid glycerin sodium sulfate); N-acyl glutamates (for example, mono sodium N-lauroylglutamate, disodium N-stearoylglutamate, and sodium N-myristoyl-L-glutamate); sulfated oils (for example, turkey red oil); POE-alkylether carboxylic acid; POE-alkylarylether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

Examples of the cationic surfactants include alkyltrimethylammonium salts (for example, stearyltrimethyl ammonium chloride and lauryltrimethyl ammonium chloride)alkylpyridinium salts (for example, cetylpyridinium chloride), distearyldimethylammonium chloride dialkyldimethylammonium salt; poly(N,N'-dimethyl3-methylene piperidinium) chloride; alkyl quaternary ammonium salts; alkyl dimethylbenzyl ammonium salts; alkyl isoquinolinium salts; dialkylmorpholine salts; POE alkyl amines; alkyl amine salts; polyamine fatty acid derivatives; amylalcohol fatty acid derivatives; benzalkonium chloride; and benzethonium chloride.

Examples of the ampholytic surfactants include: imidazoline type ampholytic surfactants (for example, 2-undecyl-N,N,N-(hydroxyethyl carboxymethyl)-2-imidazoline sodium salt and 2-cocoyl-2-imidazolinium hydroxidel-carboxyethyloxy 2 sodium salt); and betaine type surtactants (for example, 2-heptadecyl-n-carboxymethyl-n-hydroxyethyl imidazolinium betaine, lauryldimethylaminoacetic acid betaine, alkyl betaine, amide betaine, and sulfobetaine).

Examples of the hydrophilic nonionic surface active agents include: polyglycerin fatty acid esters such as hexaglyceryl monolaurate (HLB 14.5), hexaglyceryl monomyristate (HLB 11), hexyglyceryl monostearate (HLB 9.0), hexaglyceryl monooleate (HLB 9.0), decaglyceryl monolaurate (HLB 15.5), decaglyceryl monomyristate (HLB 14.0), decaglyceryl monostearate (HLB 12.0), decaglyceryl monoisostearate (HLB 12.0), decaglyceryl monooleate (HLB 12.0), decaglyceryl distearate (HLB 9.5), and decaglyceryl diisostearate (HLB 10.0);

polyoxyethylene glycerin fatty acid esters such as polyoxyethylene (hereafter abbreviated as POE) glyceryl monostearate (5) (HLB 9.5), POE (15) glyceryl monostearate (HLB 13.5), POE (5) glyceryl monooleate (HLB 9.5), and POE (15) glyceryl monooleate (HLB 14.5);

polyoxyethylene sorbitan fatty acid esters such as POE (20) sorbitan monococoate (HLB 16.9), POE (20) sorbitan monopalmitate (HLB 15.6), POE (20) sorbitan monostearate (HLB 14.9), POE (6) sorbitan monostearate (HLB 9.5), POE (20) sorbitan tristearate (HLB 10.5), POE (20) sorbitan monoisostearate (HLB 15.0), POE (20) sorbitan monooleate (HLB 15.0), POE (6) sorbitan monooleate (HLB 10.0), and POE (20) sorbitan trioleate (HLB 11.0);

polyoxyethylene sorbit fatty acid esters such as POE (6) sorbit monolaurate (HLB 15.5), POE (60) sorbit tetrastearate (HLB 13.0), POE (30) sorbit tetraoleate (HLB 11.5), POE (40) sorbit tetraoleate (HLB 12.5), and POE (60) sorbit tetraoleate (HLB 14.0);

polyoxyethylene lanolin/lanolin alcohol/beeswax derivatives such as POE (10) lanolin (HLB 12.0), POE (20) lanolin (HLB 13.0), POE (30) lanolin (HLB 15.0), POE (5) lanolin alcohol (HLB 12.5), POE (10) lanolin alcohol (HLB 15.5), POE (20) lanolin alcohol (HLB 16.0), POE (40) lanolin alcohol (HLB 17.0), and POE (20) sorbit beeswax (HLB 9.5);

polyoxyethylene castor oils/hydrogenated oils such as POE (20) castor oil (HLB 10.5), POE (40) castor oil (HLB 12.5), POE (50) castor oil (HLB 14.0), POE (60) castor oil (HLB 14.0), POE (20) hydrogenated castor oil (HLB 10.5), POE (30) hydrogenated castor oil (HLB 11.0), POE (40) hydrogenated castor oil (HLB 13.5), POE (60) hydrogenated castor oil (HLB 14.0), POE (80) hydrogenated castor oil (HLB 16.5), and POE (40) hydrogenated castor oil (100) hydrogenated castor oil (HLB 16.5);

polyoxyethylene sterols/hydrogenated sterols such as POE (5) phytosterol (HLB 9.5), POE (10) phytosterol (HLB 12.5), POE (20) phytosterol (HLB 15.5), POE (30) phytosterol (HLB 18.0), POE (25) phytostanol (HLB 14.5), and POE (30) cholestanol (HLB 17.0);

polyoxyethylene alkyl ethers such as POE (2) lauryl ether (HLB 9.5), POE (4.2) lauryl ether (HLB 11.5), POE (9) lauryl ether (HLB 14.5), POE (5.5) cetyl ether (HLB 10.5), POE (7) cetyl ether (HLB 11.5), POE (10) cetyl ether (HLB 13.5), POE (15) cetyl ether (HLB 15.5), POE (20) cetyl ether (HLB 17.0), POE (23) cetyl ether (HLB 18.0), POE (4) stearyl ether (HLB 9.0), POE (20) stearyl ether (HLB 18.0), POE (7) oleyl ether (HLB 10.5), POE (10) oleyl ether (HLB 14.5), POE (15) oleyl ether (HLB 16.0), POE (20) oleyl ether (HLB 17.0), POE (50) oleyl ether (HLB 18.0), POE (10) behenyl ether (HLB 10.0), POE (20) behenyl ether (HLB 16.5), POE (30) behenyl ether (HLB 18.0), POE (2) (c12-15) alkyl ether (HLB 9.0), POE (4) (c12-15) alkyl ether (HLB 10.5), POE (10) (c12-15) alkyl ether (HLB15.5), POE (5) secondary alkyl ether (HLB 10.5), POE (7) secondary alkyl ether (HLB 12.0), POE (9) alkyl ether (HLB 13.5), and POE (12) alkyl ether (HLB 14.5);

polyoxyethylene polyoxypropylene alkyl ethers such as polyoxyethylene (hereafter abbreviated as POE) (1) polyoxypropylene (hereafter abbreviated as POP) (4) cetyl ether (HLB 9.5), POE (10) POP (4) cetyl ether (HLB 10.5), POE (20) POP (8) cetyl ether (HLB 12.5), POE (20) POP (6) decyltetradecyl ether (HLB 11.0), and POE (30) POP (6) decyltetradecyl ether (HLB 12.0);

polyethylene glycol fatty acid esters such as polyethylene glycol (hereafter abbreviated as PEG) (10) (HLB 12.5), PEG (10) monostearate (HLB 11.0), PEG (25) monostearate (HLB 15.0), PEG (40) monostearate (HLB 17.5), PEG (45) monostearate (HLB 18.0), PEG (55) monostearate (HLB 18.0), PEG (10) monooleate (HLB 11.0), PEG distearate (HLB 16.5), and PEG diisostearate (HLB 9.5);

and polyoxyethylene glyceryl isostearates such as PEG (8) glyceryl isostearate (HLB 10.0), PEG (10) glyceryl isostearate (HLB 10.0), PEG (15) glyceryl isostearate (HLB 12.0), PEG (20) glyceryl isostearate (HLB 13.0), PEG (25) glyceryl isostearate (HLB 14.0), PEG (30) glyceryl isostearate (HLB 15.0), PEG (40) glyceryl isostearate (HLB 15.0), PEG (50) glyceryl isostearate (HLB 16.0), and PEG (60) glyceryl isostearate (HLB 16.0).

Examples of the lipophilic surfactant include POE (2) stearyl ether (HLB 4.0), self emulsified propylene glycol monostearate (HLB 4.0), glyceryl myristate (HLB 3.5), glyceryl monostearate (HLB 4.0), self emulsified glyceryl monostearate (HLB 4.0), glyceryl monoisostearate (HLB 4.0), glyceryl monooleate (HLB 2.5), hexaglyceryl tristearate (HLB 2.5), decaglyceryl pentastearate (HLB 3.5), decaglyceryl pontaisostearate (HLB 3.5), decaglyceryl pentaoleate (HLB 3.5), sorbitan monostearate (HLB 4.7), sorbitan tristearate (HLB 2.1), sorbitan monoisostearate (HLB 5.0), sorbitan sesquiisostearate (HLB 4.5), sorbitan monooleate (HLB 4.3), POE (6) sorbit hexastearate (HLB 3.0), POE (3) castor oil (HLB 3.0), PEG (2) monostearate (HLB 4.0), ethylene glycol monostearate (HLB 3.5), and PEG (2) stearate (HLB 4.5).

Examples of the humectant include polyethylene glycol, propylene glycol, glycerin, 1,3-butylene glycol, xylitol, sorbitol, maltitol, chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, chestnut rose fruit extract, yarrow extract, and sweet clover extract.

Examples of the natural water-soluble polymer include: plant-type polymers (for example, gum arabic, gum tragacanth, galactan, guar gum, carob gum, karaya gum, carrageenan, pectin, agar, quince seed (*Cyclonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

Examples of the semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymethylcellulose, sodium carboxymethyl cellulose, crystal cellulose, and cellulose powder); and alginic acid-type polymers (for example, sodium alginate and propyleneglycol alginate).

Examples of the synthetic water-soluble polymers include: vinyl polymers (for example, polyvinyl alcohol, polyvinyl methyl ether, polyvinylpyrrolidone, carboxy vinyl polymer); polyoxyethylene-type polymers (for example, a copolymer of polyethylene glycol 20,000, 40,000, or 60,000 and polyoxyethylene polyoxypropylene); acrylic polymers (for example, sodium polyacrylate, polyethylacrylate, and polyacrylamide); polyethyleneimine; and cationic polymers.

Examples of the thickeners include: gum arabic, carrageenan, karaya gum, gum tragacanth, carob gum, quince seed (*Cyclonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of the ultraviolet absorbents include the following compounds.

(1) Benzoic Acid-Type Ultraviolet Absorbents
Examples include paraminobenzoic acid (hereafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester.

(2) Anthranilic Acid-Type Ultraviolet Absorbents
Examples include homo mentyl-N-acetyl anthranilate.

(3) Salicylic Acid-Type Ultraviolet Absorbents
Examples include amyl salicylate, mentyl salicylate, homo mentyl salicylate, octyl salicylate, phenyl salicylate, benzyl salicylate, and p-isopropanol phenyl salicylate.

(4) Cinnamic Acid-Type Ultraviolet Absorbents
Examples include octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate, 2-ethylhexyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethyl hexanoyl-diparamethoxy cinnamate.

(5) Triazine-Type Ultraviolet Absorbents
For example, bisresorsinyl triazine.
More specifically, bis{[4-(2-ethylhexyloxy)-2-hydroxy]phenyl}-6-(4-methoxyphenyl)1,3,5-triazine, 2,4,6-tris {4-(2-ethylhexyloxycarbonyl)anilino}1,3,5-triazine, etc.

(6) Other Ultraviolet Absorbents
Examples include 3-(4'-methylbenzylidene)-d, 1-camphor, 3-benzylidene-d, 1-camphor, 2-phenyl-5-methyl benzoxazole, 2,2'-hydroxy-5-methylphenyl benzotriazol, 2-(2'-hydroxy-5'-t-octylphenyl) benzotriazol, 2-(2'-hydroxy-5'-methylphenyl benzotriazol, dibenzaladine, dianisoylmethane, 4-methoxy-4'-t-butyl dibenzoyl-methane, and 5-(3,3-dimethyl-2-norbornylidene)-3-pentane-2-one. Also, pyridazine derivatives such as dimorpholinopyridazinone.

Examples of the sequestering agents include 1-hydroxy ethanel-diphosphonic acid, 1-hydroxy ethanel-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

Examples of the lower alcohols include ethanol, propanol, isopropanol, isobutyl alcohol, and t-butyl alcohol.

Examples of the polyhydric alcohols include: dihydric alcohols (for example, ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, pentaerythritol such as 1,2,6-hexanetriol); pentahydric alcohols (for example, xylitol); hexahydric alcohols (for example, sorbitol, mannitol); polyhydric alcohol polymers (for example, diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethylether, ethylene glycol diethyl ether, and ethylene glycol dibutyl ether); dihydric alcohol alkylethers (for example, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycolmonomethyl ether acetate, propylene glycol monoethyl ether acetate, propylene glycol monopropyl ether acetate, and propylene glycol monophenyl ether acetate); glycerin mono alkyl ethers (for example, chimyl alcohol, selachyl alcohol, and batyl alcohol); sugar alcohols (for example, sorbitol, maltitol, maltotriose, mannitol, sucrose, erythritol, glucose, fructose, starch amylolysis sugar, maltose, xylitose, and alcohol prepared by the reduction of starch amylolysis sugar); glysolid; tetrahydro furfuryl alcohol; POE-tetrahydro furfuryl alcohol; POP-butyl ether; POP/POE-butyl ether; tripolyoxypropylene glycerin ether; POP-glycerin ether, POP-glycerin ether phosphoric acid; POP/POE-pentane erythritol ether, and polyglycerin.

Examples of the monosaccharides include: trioses (for example, D-glyceryl aldehyde and dihydroxyacetone); tetroses (for example, D-etythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose); deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

Examples of the oligosaccharides include sucrose, umbelliferose, lactose, planteose, isolignoses, α,α-trehalose, raffinose, lignoses, umbilicine, stachyose and verbascose.

Examples of the polysaccharides include cellulose, quince seed, chondroitin sulfate, starch, galactan, dermatan sulfate, glycogen, gum arabic, heparan sulfate, hyaluronic acid, traganth gum, keratan sulfate, chondroitin, xanthan gum, mucoitin sulfuric acid, guar gum, dextran, kerato sulfate, locustbean gum, succinoglucane, and charonic acid.

Examples of amino acids include neutral amino acids (for example, threonine and cysteine) and basic amino acids (for example, hydroxylysine). Examples of the amino acid derivatives include sodium acyl sarcosinate (sodium N-lauroyl sarcosinate), acyl glutamate, sodium acyl β-alanine, glutathione, and pyrrolidone carboxylic acid.

Examples of the organic amines include monoethanolamine, diethanolamine, triethanolamine, morpholine, triisopropanolamine, 2-amino-2-methyl-1,3-propanediol, and 2-amino-2-methyl-1-propanol.

Examples of polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of the pH adjustment agents include buffers such as lactic acid-sodium lactate, citric acid-sodium citrate, and succinic acid-sodium succinate.

Examples of vitamins include vitamin A, B1, B2, B6, C and E as well as their derivatives, pantothenic acid and its derivatives, and biotin.

Examples of the antioxidants include tocopherols, dibutyl hydroxytoluene, butyl hydroxyanisole, and gallic ester.

Examples of antioxidation assistants include phosphoric acid, citric acid, ascorbic acid, maleic acid, malonic acid, succinic acid, fumaric acid, cephalin, hexametaphosphate, phytic acid, and ethylene diamine tetraacetic acid.

Examples of other possible ingredients include antiseptics (methylparaben, ethylparaben, butylparaben, and phenoxyethanol); anti-inflammatory agents (for example, glycyrrhizic acid derivatives, glycyrrhetinic acid derivatives, salicylic acid derivatives, hinokitiol, zinc oxide, and allantoin); whitening agents (for example, creeping saxifrage extract and arbutin); various extracts (for example, Phellodendri Cortex, goldthread, *lithospermum* root, *Paeonia lactiflora*, *Swertia japonica*, Birch, sage, loquat, carrot, *aloe*, *Malva sylvestris*, *Iris*, grape, *Coix ma-yuen*, sponge gourd, lily, saffron, *Cnidium officinale*, sheng jiang, *Hypericum erectum*, Ononis, garlic, Guinea pepper, chen pi, *Ligusticum acutilobum*, and seaweed), activators (royal jelly, photosensitive substances, and cholesterol derivatives); blood circulation promoting agents (for example, nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and γ-orizanol); anti-seborrhea agents (for example, sulfur and thiantol); and antiinflammatory agents (for example, tranexamic acid, thiotaurine, and hypotaurine).

The product form of the sunscreen cosmetic of the present invention is not limited. Examples include creams, emulsions, and lotions, and creams are preferable in terms of stability and the sensation during use.

EXAMPLES

Preparation Method

Using the formulations shown in the tables, the 0 part, heated up to 85° C. and melted, was mixed into the W part, which had been heated up to 75° C. and dissolved, and emulsified; the P part was mixed into this and quickly cooled down to 30° C. (refer to the table for the relationship between the ingredients and the parts) to prepare an oil-in-water emulsified sunscreen cosmetic. The following evaluation tests were conducted.

In the part column of the tables, W denotes water phase ingredients, O denotes oil phase ingredients, and P denotes powder ingredients.

1. High Temperature Stability

The cosmetics were put into glass tubes and stored in thermostatic baths set to 50° C., 40° C., and 25° C. for one month; after one month they were checked for separation. Stability was evaluated based on the following criteria.

⊚: No separation is observed under any storage conditions.

○: Those stored at 50° C. are separated, but separation is not observed with other temperature conditions.

Δ: Those stored at 50° C. and 40° C. are separated, but no separation is observed with those stored at 25° C.

X: Separation is observed under all the conditions.

2. Stability Under Temperature Cycling

The cosmetics were put into glass tubes and stored under temperature cycling (5° C.-45° C., 2 cycles/day, holding at 5° C. and 45° C. for two hours); after two weeks, one month, and two months, they were compared with those stored at 25° C. To compare the states of the samples, they were applied thinly on a black board and smoothness was evaluated.

⊚: No difference even with those stored for two months.

○: No difference up to one month, but those stored for two months exhibit unevenness.

Δ: No difference up to two weeks, but those stored for one month exhibit unevenness.

X: Those stored for two weeks exhibit unevenness.

3. Emulsified Particle Size

The emulsified particle size of the cosmetics immediately after preparation was evaluated by means of microscopic observation.

⊚: 1 micrometer or less

○: Mostly 1 micrometer or less, although some emulsified particles having a size of 2-3 micrometers are observed Δ: Mostly 3 micrometers or less, with many particles having a size of 1 micrometer or more X: Many emulsified particles having a size of 3 micrometers or more are observed.

4. pH

The pH of the cosmetics immediately after the preparation was measured by using a HORIBA pH Meter F-13 (from HORIBA, Ltd.).

5. Sensation During Use (Absorption)

A panel of 10 specialists applied the cosmetics on their faces and judged the sensation of good absorption during use based on the following criteria.

⊚: 9 or more panelists reported good absorption.

○: 6 or more and less than 9 panelists reported good absorption.

Δ: 4 or more and less than 6 panelists reported good absorption.

X: Less than 4 panelists reported good absorption.

6. Sensation During Use (Stickiness)

A panel of 10 specialists applied the cosmetics on their faces and judged the non-sticky sensation after application based on the following criteria.

⊚: 9 or more panelists reported non-stickiness.

○: 6 or more and less than 9 panelists reported non-stickiness.

Δ: 4 or more and less than 6 panelists reported non-stickiness.

X: Less than 4 panelists reported non-stickiness.

7. Low Temperature Stability

The cosmetics were put into glass tubes and stored for three months at −20° C.; after one month a polarizing microscope was used to check whether or not crystals had precipitated; the evaluation was conducted based on the following criteria.

○: No crystalline precipitation is observed.
X: Crystalline precipitation is observed.

The following tables show the formulations of the cosmetics and the aforementioned evaluation results. In the formulations, prior art cosmetic raw materials and the following commercial products were used.

PEG40 stearate: NIKKOL MYS-40V (Nikko Chemicals Co., Ltd.)
PEG100 stearate: NIKKOL MYS-100V (Nikko Chemicals Co., Ltd.)
Sorbitan tristearate: NIKKOL SS-30V (Nikko Chemicals Co., Ltd.)
Self emulsified glyceryl stearate: Tegin TV (Nikko Chemicals Co., Ltd.)
Tert-butylmethoxybenzoylmethane: Parsol 1789 (DSM Nutrition Japan Co., Ltd.)
Bis ethylhexyloxyphenol methoxyphenyl Triazine: Tinosorb S (Ciba Specialty Chemicals Co., Ltd.)
Octocrylene: Parsol 340 (DSM Nutrition Japan Co., Ltd.)
Ethylhexyl methoxycinnamate: Parsol MCX (DSM Nutrition Japan Co., Ltd.)
Phenylbenzimidazolesulfonic acid: Eusolex 232 (Merck)
2-ethylhexyl 2-ethylhexanoate: KAK88SX (Kokyu Alcohol Kogyo Co., Ltd.)
Isononyl isononanoate: KAK99SX (Kokyu Alcohol Kogyo Co., Ltd.)
Carnosine: Dragosine 2/060700 (Symrise)
Myristyl myristate: Crodamol. MM-P (Croda Japan KK)
Dimeticone: KF-96A-6T (Shin-Etsu Chemical Co., Ltd.)
Titanium oxide: Titanium Oxide MT-062 (Tayca Corporation)

Example 1 and Comparative examples 1-1, 1-2, and 1-3

TABLE 1-1

| | | | Condition (A) in claim 1 | | | |
| --- | --- | --- | --- | --- | --- | --- |
| Part | | Ingredient | Example 1 | Comparative example 1-1 | Comparative example 1-2 | Comparative example 1-3 |
| O | A-1 | PEG40 stearate | 1.1 | 2.5 | — | 1.6 |
| O | | PEG100 stearate | — | — | — | — |
| O | A-2 | Sorbitan tristearate | 1 | 1.1 | 1 | — |
| O | A-3 | Self emulsified glyceryl stearate | 2.5 | — | 3.6 | 3 |
| O | B | Tert-butylmethoxybenzoylmethane | 2 | 2 | 2 | 2 |
| O | | Bis ethylhexyloxyphenol methoxyphenyl triazine | 0.5 | 0.5 | 0.5 | 0.5 |
| O | C | Octocrylene | 5 | 5 | 5 | 5 |
| O | | Ethylhexyl methoxycinnamate | — | — | — | — |
| W | D | Phenylbenzimidazolesulfonic acid | 2 | 2 | 2 | 2 |
| O | E | Stearyl alcohol | 0.5 | 0.5 | 0.5 | 0.5 |
| O | | Behenyl alcohol | 2 | 2 | 2 | 2 |
| O | | Cetanol | — | — | — | — |
| O | F | 2-ethyhexyl 2-ethylhexanoate | — | — | — | — |
| O | | Isononyl isononanoate | — | — | — | — |
| W | G | PEG/PPG-14/7 dimethyl ether | — | — | — | — |
| W | | PEG/PPG-17/4 dimethyl ether | — | — | — | — |
| W | H | Carnosine | — | — | — | — |
| W | Other | Glycerin | 7 | 7 | 7 | 7 |
| W | | Dipropylene glycol | 5 | 5 | 5 | 5 |
| W | | Butylene glycol | 8 | 8 | 8 | 8 |
| W | | Xanthan gum | 0.15 | 0.15 | 0.15 | 0.15 |
| O | | Myristyl myristate | 2 | 2 | 2 | 2 |
| O | | Microcrystalline wax | 1 | 1 | 1 | 1 |
| O | | Dimeticone | 3 | 3 | 3 | 3 |
| O | | Squalane | 5 | 5 | 5 | 5 |
| W | | Triethanolamine | 1.2 | 1.2 | 1.2 | 1.2 |
| P | | Titanium oxide | 1 | 1 | 1 | 1 |
| P | | Spherical cellulose | 0.5 | 0.5 | 0.5 | 0.5 |
| W | | Edetate | 0.1 | 0.1 | 0.1 | 0.1 |
| W | | Phenoxy ethanol | 0.5 | 0.5 | 0.5 | 0.5 |
| W | | Sodium pyrosulfite | 0.003 | 0.003 | 0.003 | 0.003 |
| W | | Hexametaphosphoric soda | 0.1 | 0.1 | 0.1 | 0.1 |
| P | | Iron oxide (red) | 0.0003 | 0.0003 | 0.0003 | 0.0003 |
| P | | Iron oxide (yellow) | 0.006 | 0.006 | 0.006 | 0.006 |
| W | | Water | Balance | Balance | Balance | Balance |
| | | High temperature stability | ○ | X | X | Δ |
| | | Emulsified particle size | ○ | X | X | Δ |
| | | Low temperature stability | ○ | — | — | — |
| | | pH | 7.4 | — | — | — |
| | | Sensation during use (stickiness) | ○ | — | — | X |
| | | Sensation during use (absorption) | ○ | — | — | X |

Table 1-1 shows the results of checking condition (A) in claim 1.

When any of ingredients A-1, A-2, and A-3 is removed (Comparative examples 1-1 to 1-3), the stability and usability deteriorate.

In particular, when A-1 or A-3 is removed (Comparative examples 1-1 and 1-2), emulsified products that can be evaluated for the sensation during use are not formed to begin with.

Examples 1, 3, and 4, and Comparative examples 1-4

TABLE 1-2

| | | | Condition (B) in claim 1 | | | |
|---|---|---|---|---|---|---|
| Part | Ingredient | | Example 1 | Example 3 | Example 4 | Comparative example 1-4 |
| O | A-1 | PEG40 stearate | 1.1 | 1.1 | 1.1 | 1.1 |
| O | | PEG100 stearate | — | — | — | — |
| O | A-2 | Sorbitan tristearate | 1 | 1 | 1 | 1 |
| O | A-3 | Self emulsified glyceryl stearate | 2.5 | 2.5 | 2.5 | 2.5 |
| O | B | Tert-butylmethoxybenzoylmethane | 2 | 1 | 2 | 3 |
| O | | Bis ethylhexyloxyphenol methoxyphenyl triazine | 0.5 | 0.5 | 2 | 3 |
| O | C | Octocrylene | 5 | 5 | 5 | 5 |
| O | | Ethylhexyl methoxycinnamate | — | — | — | — |
| W | D | Phenylbenzimidazolesulfonic acid | 2 | 2 | 2 | 2 |
| O | E | Stearyl alcohol | 0.5 | 0.5 | 0.5 | 0.5 |
| O | | Behenyl alcohol | 2 | 2 | 2 | 2 |
| O | | Cetanol | — | — | — | — |
| O | F | 2-ethylhexyl 2-ethylhexanoate | — | — | — | — |
| O | | Isononyl isononanoate | — | — | — | — |
| W | G | PEG/PPG-14/7 dimethyl ether | — | — | — | — |
| W | | PEG/PPG-17/4 dimethyl ether | — | — | — | — |
| W | H | Carnosine | — | — | — | — |
| W | Other | Glycerin | 7 | 7 | 7 | 7 |
| W | | Dipropylene glycol | 5 | 5 | 5 | 5 |
| W | | Butylene glycol | 8 | 8 | 8 | 8 |
| W | | Xanthan gum | 0.15 | 0.15 | 0.15 | 0.15 |
| O | | Myristyl myristate | 2 | 2 | 2 | 2 |
| O | | Microcrystalline wax | 1 | 1 | 1 | 1 |
| O | | Dimeticone | 3 | 4 | 3 | 3 |
| O | | Squalane | 5 | 5 | 3.5 | 1.5 |
| W | | Triethanolamine | 1.2 | 1.2 | 1.2 | 1.2 |
| P | | Titanium oxide | 1 | 1 | 1 | 1 |
| P | | Spherical cellulose | 0.5 | 0.5 | 0.5 | 0.5 |
| W | | Edetate | 0.1 | 0.1 | 0.1 | 0.1 |
| W | | Phenoxy ethanol | 0.5 | 0.5 | 0.5 | 0.5 |
| W | | Sodium pyrosulfite | 0.003 | 0.003 | 0.003 | 0.003 |
| W | | Hexametaphosphoric soda | 0.1 | 0.1 | 0.1 | 0.1 |
| P | | Iron oxide (red) | 0.0003 | 0.0003 | 0.0003 | 0.0003 |
| P | | Iron oxide (yellow) | 0.006 | 0.006 | 0.006 | 0.006 |
| W | | Water | Balance | Balance | Balance | Balance |
| | | High temperature stability | ○ | ○ | ○ | ○ |
| | | Emulsified particle size | ○ | ○ | ○ | ○ |
| | | Low temperature stability | ○ | ○ | ○ | X |
| | | pH | 7.4 | 7.4 | 7.4 | 7.4 |
| | | Sensation during use (Stickiness) | ○ | ○ | ○ | ○ |
| | | Sensation during use (absorption) | ○ | ○ | ○ | ○ |

Table 1-2 shows the results of checking condition (B) in claim 1.

The low temperature stability deteriorates when the amount of the ingredients used in (B) is increased (Comparative example 1-4).

Examples 1, 2, 5, and 6 and Comparative examples 1-5 to 1-6

TABLE 1-3

| | | | | | Condition (C) in claim 1 | | | |
| --- | --- | --- | --- | --- | --- | --- | --- | --- |
| Part | Ingredient | | Example 1 | Example 2 | Example 5 | Example 6 | Comparative example 1-5 | Comparative example 1-6 |
| O | A-1 | PEG40 stearate | 1.1 | — | 1.1 | 1.1 | 1.1 | 1.1 |
| O | | PEG100 stearate | — | 1 | — | — | — | — |
| O | A-2 | Sorbitan tristearate | 1 | 1.1 | 1 | 1 | 1 | 1 |
| O | A-3 | Self emulsified glyceryl stearate | 2.5 | 2.5 | 2.5 | 2.5 | 2.5 | 2.5 |
| O | B | Tert-butylmethoxybenzoylmethane | 2 | 2 | 2 | 2 | 2 | 1 |
| O | | Bis ethylhexyloxyphenol methoxyphenyl triazine | 0.5 | 0.5 | 0.5 | 0.5 | 0.5 | 0.5 |
| O | C | Octocrylene | 5 | 3 | 2 | 5 | — | 5 |
| O | | Ethylhexyl methoxycinnamate | — | 5 | 1 | 5 | — | 10 |
| W | D | Phenylbenzimidazolesulfonic acid | 2 | 2 | 2 | 2 | 2 | 2 |
| O | E | Stearyl alcohol | 0.5 | 1 | 0.5 | 0.5 | 0.5 | 0.5 |
| O | | Behenyl alcohol | 2 | 0.5 | 2 | 2 | 2 | 2 |
| O | | Cetanol | — | 1 | — | — | — | — |
| O | F | 2-ethyhexyl 2-ethylhexanoate | — | — | — | — | — | — |
| O | | Isononyl isononanoate | — | — | — | — | — | — |
| W | G | PEG/PPG-14/7 dimethyl ether | — | — | — | — | — | — |
| W | | PEG/PPG-17/4 dimethyl ether | — | — | — | — | — | — |
| W | H | Carnosine | — | — | — | — | — | — |
| W | Other | Glycerin | 7 | 7 | 7 | 7 | 7 | 7 |
| W | | Dipropylene glycol | 5 | 5 | 5 | 5 | 5 | 5 |
| W | | Butylene glycol | 8 | 8 | 8 | 8 | 8 | 8 |
| W | | Xanthan gum | 0.15 | 0.15 | 0.15 | 0.15 | 0.15 | 0.15 |
| O | | Myristyl myristate | 2 | 2 | 2 | 2 | 2 | 1 |
| O | | Microcrystalline wax | 1 | 1 | 1 | 1 | 1 | 1 |
| O | | Dimeticone | 3 | 3 | 5 | 2 | 7 | — |
| O | | Squalane | 5 | 2 | 5 | 1 | 6 | — |
| W | | Triethanolamine | 1.2 | 1.2 | 1.2 | 1.2 | 1.2 | 1.2 |
| P | | Titanium oxide | 1 | 1 | 1 | 1 | 1 | 1 |
| P | | Spherical cellulose | 0.5 | 0.5 | 0.5 | 0.5 | 0.5 | 0.5 |
| W | | Edetate | 0.1 | 0.1 | 0.1 | 0.1 | 0.1 | 0.1 |
| W | | Phenoxy ethanol | 0.5 | 0.5 | 0.5 | 0.5 | 0.5 | 0.5 |
| W | | Sodium pyrosulfite | 0.003 | 0.003 | 0.003 | 0.003 | 0.003 | 0.003 |
| W | | Hexametaphosphoric soda | 0.1 | 0.1 | 0.1 | 0.1 | 0.1 | 0.1 |
| P | | Iron oxide (red) | 0.0003 | 0.0003 | 0.0003 | 0.0003 | 0.0003 | 0.0003 |
| P | | Iron oxide (yellow) | 0.006 | 0.006 | 0.006 | 0.006 | 0.006 | 0.006 |
| W | | Water | Balance | Balance | Balance | Balance | Balance | Balance |
| | | High temperature stability | ○ | ○ | ○ | ○ | ○ | X |
| | | Emulsified particle size | ○ | ○ | ○ | ○ | ○ | ○ |
| | | Low temperature stability | ○ | ○ | ○ | ○ | X | ○ |
| | | pH | 7.4 | 7.4 | 7.4 | 7.4 | 7.4 | 7.4 |
| | | Sensation during use (stickiness) | ○ | ○ | ○ | ○ | ◎ | X |
| | | Sensation during use (absorption) | ○ | ○ | ○ | ○ | ○ | ○ |

Table 1-3 shows the results of checking condition (C) in claim 1.

The low temperature stability deteriorates when the amount of the ingredients used in (C) is decreased (removed in Comparative example 1-5). The high temperature stability deteriorates when the amount is increased (Comparative example 1-6).

Examples 1, 7, and 8 and Comparative examples 1-7 to 1-8

TABLE 1-4

| | | | Condition (D) in claim 1 | | | | |
|---|---|---|---|---|---|---|---|
| Part | Ingredient | | Example 1 | Example 7 | Example 8 | Comparative example 1-7 | Comparative example 1-8 |
| O | A-1 | PEG40 stearate | 1.1 | 1.1 | 1.1 | 1.1 | 1.1 |
| O | | PEG100 stearate | — | — | — | — | — |
| O | A-2 | Sorbitan tristearate | 1 | 1 | 1 | 1 | 1 |
| O | A-3 | Self emulsified glyceryl stearate | 2.5 | 2.5 | 2.5 | 2.5 | 2.5 |
| O | B | Tert-butylmethoxybenzoylmethane | 2 | 2 | 2 | 2 | 2 |
| O | | Bis ethylhexyloxyphenol methoxyphenyl triazine | 0.5 | 0.5 | 0.5 | 0.5 | 0.5 |
| O | C | Octocrylene | 5 | 5 | 5 | 5 | 5 |
| O | | Ethylhexyl methoxycinnamate | — | — | — | — | — |
| W | D | Phenylbenzimidazolesulfonic acid | 2 | 1 | 3 | 0.01 | 6 |
| O | E | Stearyl alcohol | 0.5 | 0.5 | 0.5 | 0.5 | 0.5 |
| O | | Behenyl alcohol | 2 | 2 | 2 | 2 | 2 |
| O | | Cetanol | — | — | — | — | — |
| O | F | 2-ethylhexyl 2-ethylhexanoate | — | — | — | — | — |
| O | | Isononyl isononanoate | — | — | — | — | — |
| W | G | PEG/PPG-14/7 dimethyl ether | — | — | — | — | — |
| W | | PEG/PPG-17/4 dimethyl ether | — | — | — | — | — |
| W | H | Carnosine | — | — | — | — | — |
| W | Other | Glycerin | 7 | 7 | 7 | 7 | 7 |
| W | | Dipropylene glycol | 5 | 5 | 5 | 5 | 5 |
| W | | Butylene glycol | 8 | 8 | 8 | 8 | 8 |
| W | | Xanthan gum | 0.15 | 0.15 | 0.15 | 0.15 | 0.15 |
| O | | Myristyl myristate | 2 | 2 | 2 | 2 | 2 |
| O | | Microcrystalline wax | 1 | 1 | 1 | 1 | 1 |
| O | | Dimeticone | 3 | 3 | 3 | 3 | 3 |
| O | | Squalane | 5 | 5 | 5 | 5 | 5 |
| W | | Triethanolamine | 1.2 | 0.6 | 1.8 | 0.006 | 3.6 |
| P | | Titanium oxide | 1 | 1 | 1 | 1 | 1 |
| P | | Spherical cellulose | 0.5 | 0.5 | 0.5 | 0.5 | 0.5 |
| W | | Edetate | 0.1 | 0.1 | 0.1 | 0.1 | 0.1 |
| W | | Phenoxy ethanol | 0.5 | 0.5 | 0.5 | 0.5 | 0.5 |
| W | | Sodium pyrosulfite | 0.003 | 0.003 | 0.003 | 0.003 | 0.003 |
| W | | Hexametaphosphoric soda | 0.1 | 0.1 | 0.1 | 0.1 | 0.1 |
| P | | Iron oxide (red) | 0.0003 | 0.0003 | 0.0003 | 0.0003 | 0.0003 |
| P | | Iron oxide (yellow) | 0.006 | 0.006 | 0.006 | 0.006 | 0.006 |
| W | | Water | Balance | Balance | Balance | Balance | Balance |
| | | High temperature stability | ○ | ○ | ○ | ○ | ○ |
| | | Emulsified particle size | ○ | ○ | ○ | Δ | ○ |
| | | Low temperature stability | ○ | ○ | ○ | ○ | ○ |
| | | pH | 7.4 | 7.4 | 7.4 | 7.4 | 7.4 |
| | | Sensation during use (stickiness) | ○ | ○ | ○ | ○ | Δ |
| | | Sensation during use (absorption) | ○ | ○ | ○ | Δ | ○ |

Table 1-4 shows the results of checking condition (D) in claim 1.

The low temperature stability deteriorates when the amount of the ingredients used in (D) is decreased (Comparative example 1-7). The sensation during use deteriorates when the amount is increased (Comparative example 1-8).

Examples 1, 9, and 10 and Comparative examples 2-1 to 2-2

TABLE 2-1

| | | | Condition (A) in claim 1 | | | | |
|---|---|---|---|---|---|---|---|
| Part | Ingredient | | Example 1 | Comparative example 2-1 | Example 9 | Example 10 | Comparative example 2-2 |
| O | A-1 | PEG40 stearate | 1.1 | 0.11 | 0.44 | 1.32 | 1.54 |
| O | A-2 | Sorbitan tristearate | 1 | 0.1 | 0.4 | 1.2 | 1.4 |
| O | A-3 | Self emulsified glyceryl stearate | 2.5 | 0.25 | 1 | 3 | 3.5 |
| O | B | Tert-butylmethoxybenzoylmethane | 2 | 2 | 2 | 2 | 2 |
| O | | Bis ethylhexyloxyphenol methoxyphenyl triazine | 0.5 | 0.5 | 0.5 | 0.5 | 0.5 |
| O | C | Octocrylene | 5 | 5 | 5 | 5 | 5 |
| O | | Ethylhexyl methoxycinnamate | — | — | — | — | — |
| W | D | Phenylbenzimidazolesulfonic acid | 2 | 2 | 2 | 2 | 2 |
| O | E | Stearyl alcohol | 0.5 | 0.5 | 0.5 | 0.5 | 0.5 |
| O | | Behenyl alcohol | 2 | 2 | 2 | 2 | 2 |
| O | | Cetanol | — | — | — | — | — |
| O | F | 2-ethyhexyl 2-ethylhexanoate | — | — | — | — | — |
| O | | Isononyl isononanoate | — | — | — | — | — |
| W | G | PEG/PPG-14/7 dimethyl ether | — | — | — | — | — |
| W | | PEG/PPG-17/4 dimethyl ether | — | — | — | — | — |
| W | H | Carnosine | — | — | — | — | — |
| W | Other | Glycerin | 7 | 7 | 7 | 7 | 7 |
| W | | Dipropylene glycol | 5 | 5 | 5 | 5 | 5 |
| W | | Butylene glycol | 8 | 8 | 8 | 8 | 8 |
| W | | Xanthan gum | 0.15 | 0.15 | 0.15 | 0.15 | 0.15 |
| O | | Myristyl myristate | 2 | 2 | 2 | 2 | 2 |
| O | | Microcrystalline wax | 1 | 1 | 1 | 1 | 1 |
| O | | Dimeticone | 3 | 3 | 3 | 3 | 3 |
| O | | Squalane | 5 | 5 | 5 | 5 | 5 |
| W | | Triethanolamine | 1.2 | 1.2 | 1.2 | 1.2 | 1.2 |
| P | | Titanium oxide | 1 | 1 | 1 | 1 | 1 |
| P | | Spherical cellulose | 0.5 | 0.5 | 0.5 | 0.5 | 0.5 |
| W | | Edetate | 0.1 | 0.1 | 0.1 | 0.1 | 0.1 |
| W | | Phenoxy ethanol | 0.5 | 0.5 | 0.5 | 0.5 | 0.5 |
| W | | Sodium pyrosulfite | 0.003 | 0.003 | 0.003 | 0.003 | 0.003 |
| W | | Hexametaphosphoric soda | 0.1 | 0.1 | 0.1 | 0.1 | 0.1 |
| P | | Iron oxide (red) | 0.0003 | 0.0003 | 0.0003 | 0.0003 | 0.0003 |
| P | | Iron oxide (yellow) | 0.006 | 0.006 | 0.006 | 0.006 | 0.006 |
| W | | Water | Balance | Balance | Balance | Balance | Balance |
| | Condition in claim 2 | (A-1) + (A-2) + (A-3) | 4.6 | 0.46 | 1.84 | 5.52 | 6.44 |
| | | (A-3)/(A-1) + (A-2) + (A-3) | 0.5435 | 0.5435 | 0.5435 | 0.5435 | 0.5435 |
| | | E/(A-1) + (A-2) + (A-3) | 0.5435 | 5.4348 | 1.3587 | 0.4529 | 0.3882 |
| | | High temperature stability | ○ | X | ○ | ◎ | ◎ |
| | | Cycling stability | ○ | — | — | — | — |
| | | Sensation during use (stickiness) | ○ | ◎ | ○ | ○ | Δ |
| | | Sensation during use (absorption) | ○ | ○ | ○ | ○ | ○ |

Table 2-1 shows the results of checking for the total of A-1 to A-3 in claim 1.

When the total of these ingredients decreases, the high temperature stability deteriorates (Comparative example 2-1). The sensation during use deteriorates when the amount is increased (Comparative example 2-2).

Examples 1 and 11, and Comparative examples 2-3 to 2-4

TABLE 2-2

| | | | Condition (1) in claim 2 | | | |
|---|---|---|---|---|---|---|
| Part | Ingredient | | Example 1 | Comparative example 2-3 | Example 11 | Comparative example 2-4 |
| O | A-1 | PEG40 stearate | 1.1 | 2.2 | 0.85 | 0.6 |
| O | A-2 | Sorbitan tristearate | 1 | 2 | 0.75 | 0.5 |
| O | A-3 | Self emulsified glyceryl stearate | 2.5 | 0.4 | 3 | 3.5 |
| O | B | Tert-butylmethoxybenzoylmethane | 2 | 2 | 2 | 2 |
| O | | Bis ethylhexyloxyphenol methoxyphenyl triazine | 0.5 | 0.5 | 0.5 | 0.5 |
| O | C | Octocrylene | 5 | 5 | 5 | 5 |
| O | | Ethylhexyl methoxycinnamate | — | — | — | — |
| W | D | Phenylbenzimidazolesulfonic acid | 2 | 2 | 2 | 2 |
| O | E | Stearyl alcohol | 0.5 | 0.5 | 0.5 | 0.5 |
| O | | Behenyl alcohol | 2 | 2 | 2 | 2 |
| O | | Cetanol | — | — | — | — |
| O | F | 2-ethyhexyl 2-ethylhexanoate | — | — | — | — |
| O | | Isononyl isononanoate | — | — | — | — |
| W | G | PEG/PPG-14/7 dimethyl ether | — | — | — | — |
| W | | PEG/PPG-17/4 dimethyl ether | — | — | — | — |
| W | H | Carnosine | — | — | — | — |
| W | Other | Glycerin | 7 | 7 | 7 | 7 |
| W | | Dipropylene glycol | 5 | 5 | 5 | 5 |
| W | | Butylene glycol | 8 | 8 | 8 | 8 |
| W | | Xanthan gum | 0.15 | 0.15 | 0.15 | 0.15 |
| O | | Myristyl myristate | 2 | 2 | 2 | 2 |
| O | | Microcrystalline wax | 1 | 1 | 1 | 1 |
| O | | Dimeticone | 3 | 3 | 3 | 3 |
| O | | Squalane | 5 | 5 | 5 | 5 |
| W | | Triethanolamine | 1.2 | 1.2 | 1.2 | 1.2 |
| P | | Titanium oxide | 1 | 1 | 1 | 1 |
| P | | Spherical cellulose | 0.5 | 0.5 | 0.5 | 0.5 |
| W | | Edetate | 0.1 | 0.1 | 0.1 | 0.1 |
| W | | Phenoxy ethanol | 0.5 | 0.5 | 0.5 | 0.5 |
| W | | Sodium pyrosulfite | 0.003 | 0.003 | 0.003 | 0.003 |
| W | | Hexametaphosphoric soda | 0.1 | 0.1 | 0.1 | 0.1 |
| P | | Iron oxide (red): | 0.0003 | 0.0003 | 0.0003 | 0.0003 |
| P | | Iron oxide (yellow): | 0.006 | 0.006 | 0.006 | 0.006 |
| W | | Water | Balance | Balance | Balance | Balance |
| | Condition in claim 2 | (A-1) + (A-2) + (A-3) | 4.6 | 4.6 | 4.6 | 4.6 |
| | | (A-3)/(A-1) + (A-2) + (A-3) | 0.5435 | 0.087 | 0.6522 | 0.7609 |
| | | E/(A-1) + (A-2) + (A-3) | 0.5435 | 0.5435 | 0.5435 | 0.5435 |
| | | High temperature stability | ○ | Δ | ○ | Δ |
| | | Cycling stability | ○ | Δ | ○ | Δ |
| | | Sensation during use (stickiness) | ○ | ○ | ○ | Δ |
| | | Sensation during use (absorption) | ○ | ○ | ○ | Δ |

Table 2-2 shows the results of checking condition (1) in claim 2.

When the ratio of A-3 to the total amount of A-1 to A-3 is low, the stability deteriorates (Comparative example 2-3). When this ratio is high, the sensation during use and stability deteriorate (Comparative example 2-4).

Examples 1, 12, and 13 and Comparative examples 2-5 to 2-6

TABLE 2-3

| | | | | Condition (2) in claim 2 | | | |
|---|---|---|---|---|---|---|---|
| Part | Ingredient | | Example 1 | Comparative example 2-5 | Example 12 | Example 13 | Comparative example 2-6 |
| O | A-1 | PEG40 stearate | 1.1 | 1.1 | 1.1 | 1.1 | 1.1 |
| O | A-2 | Sorbitan tristearate | 1 | 1 | 1 | 1 | 1 |
| O | A-3 | Self emulsified glyceryl stearate | 2.5 | 2.5 | 2.5 | 2.5 | 2.5 |
| O | B | Tert-butylmethoxybenzoylmethane | 2 | 2 | 2 | 2 | 2 |
| O | | Bis ethylhexyloxyphenol methoxyphenyl triazine | 0.5 | 0.5 | 0.5 | 0.5 | 0.5 |
| O | C | Octocrylene | 5 | 5 | 5 | 5 | 5 |
| O | | Ethylhexyl methoxycinnamate | — | — | — | — | — |
| W | D | Phenylbenzimidazolesulfonic acid | 2 | 2 | 2 | 2 | 2 |
| O | E | Stearyl alcohol | 0.5 | 0.15 | 0.3 | 0.6 | 1 |
| O | | Behenyl alcohol | 2 | 1 | 1.5 | 2.4 | 4 |
| O | | Cetanol | — | — | — | — | — |
| O | F | 2-ethyhexyl 2-ethylhexanoate | — | — | — | — | — |
| O | | Isononyl isononanoate | — | — | — | — | — |
| W | G | PEG/PPG-14/7 dimethyl ether | — | — | — | — | — |
| W | | PEG/PPG-17/4 dimethyl ether | — | — | — | — | — |
| W | H | Carnosine | — | — | — | — | — |
| W | Other | Glycerin | 7 | 7 | 7 | 7 | 7 |
| W | | Dipropylene glycol | 5 | 5 | 5 | 5 | 5 |
| W | | Butylene glycol | 8 | 8 | 8 | 8 | 8 |
| W | | Xanthan gum | 0.15 | 0.15 | 0.15 | 0.15 | 0.15 |
| O | | Myristyl myristate | 2 | 2 | 2 | 2 | 2 |
| O | | Microcrystalline wax | 1 | 1 | 1 | 1 | 1 |
| O | | Dimeticone | 3 | 3 | 3 | 3 | 3 |
| O | | Squalane | 5 | 5 | 5 | 5 | 5 |
| W | | Triethanolamine | 1.2 | 1.2 | 1.2 | 1.2 | 1.2 |
| P | | Titanium oxide | 1 | 1 | 1 | 1 | 1 |
| P | | Spherical cellulose | 0.5 | 0.5 | 0.5 | 0.5 | 0.5 |
| W | | Edetate | 0.1 | 0.1 | 0.1 | 0.1 | 0.1 |
| W | | Phenoxy ethanol | 0.5 | 0.5 | 0.5 | 0.5 | 0.5 |
| W | | Sodium pyrosulfite | 0.003 | 0.003 | 0.003 | 0.003 | 0.003 |
| W | | Hexametaphosphoric soda | 0.1 | 0.1 | 0.1 | 0.1 | 0.1 |
| P | | Iron oxide (red) | 0.0003 | 0.0003 | 0.0003 | 0.0003 | 0.0003 |
| P | | Iron oxide (yellow) | 0.006 | 0.006 | 0.006 | 0.006 | 0.006 |
| W | | Water | Balance | Balance | Balance | Balance | Balance |
| | Condition | (A-1) + (A-2) + (A-3) | 4.6 | 4.6 | 4.6 | 4.6 | 4.6 |
| | in claim 2 | (A-3)/(A-1) + (A-2) + (A-3) | 0.5435 | 0.5435 | 0.5435 | 0.5435 | 0.5435 |
| | | E/(A-1) + (A-2) + (A-3) | 0.5435 | 0.25 | 0.3913 | 0.6522 | 1.087 |
| | | High temperature stability | ◯ | X | ◯ | ◎ | ◎ |
| | | Cycling stability | ◯ | ◎ | ◎ | ◯ | △ |
| | | Sensation during use (stickiness) | ◯ | ◯ | ◯ | ◯ | ◯ |
| | | Sensation during use (absorption) | ◯ | ◯ | ◯ | ◯ | △ |

Table 2-3 shows the results of checking condition (2) in claim 2.

When the ratio of ingredient E to the total amount of A-1 to A-3 is low, the stability deteriorates (Comparative example 2-5). When this ratio is high, the cycling stability and the sensation during use (absorption) deteriorate (Comparative example 2-6).

Example 1, Examples 14-17, and Comparative examples 3-1 to 3-2

TABLE 3-1

| Part | Ingredient | | Conditions of claim 3 | | | | | | |
|------|-----|------|------|------|------|------|------|------|------|
| | | | Example 1 | Comparative example 3-1 | Example 14 | Example 15 | Example 16 | Example 17 | Comparative example 3-2 |
| O | A-1 | PEG40 stearate | 1.1 | 1.1 | 1.1 | 1.1 | 1.1 | 1.1 | 1.1 |
| O | A-2 | Sorbitan tristearate | 1 | 1 | 1 | 1 | 1 | 1 | 1 |
| O | A-3 | Self emulsified glyceryl stearate | 2.5 | 2.5 | 2.5 | 2.5 | 2.5 | 2.5 | 2.5 |
| O | B | Tert-butylmethoxybenzoylmethane | 2 | 2 | 2 | 2 | 2 | 2 | 1 |
| O | | Bis ethylhexyloxyphenol methoxyphenyl triazine | 0.5 | 0.5 | 0.5 | 0.5 | 0.5 | 0.5 | 0.5 |
| O | C | Octocrylene | 5 | 5 | 5 | 5 | 5 | 5 | 2 |
| O | | Ethylhexyl methoxycinnamate | — | — | — | — | — | — | — |
| W | D | Phenylbenzimidazolesulfonic acid | 2 | 2 | 2 | 2 | 2 | 2 | 2 |
| O | E | Stearyl alcohol | 0.5 | 0.5 | 0.5 | 0.5 | 0.5 | 0.5 | 0.5 |
| O | | Behenyl alcohol | 2 | 2 | 2 | 2 | 2 | 2 | 2 |
| O | | Cetanol | — | — | — | — | — | — | — |
| O | F | 2-ethylhexyl 2-ethylhexanoate | — | 0.1 | 1 | 2 | — | 5 | 10 |
| O | | Isononyl Isononanoate | — | — | — | — | 2 | — | — |
| W | G | PEG/PPG-14/7 dimethyl ether | — | — | — | — | — | — | — |
| W | | PEG/PPG-17/4 dimethyl ether | — | — | — | — | — | — | — |
| W | H | Carnosine | — | — | — | — | — | — | — |
| W | Other | Glycerin | 7 | 7 | 7 | 7 | 7 | 7 | 7 |
| W | | Dipropylene glycol | 5 | 5 | 5 | 5 | 5 | 5 | 5 |
| W | | Butylene glycol | 8 | 8 | 8 | 8 | 8 | 8 | 8 |
| W | | Xanthan gum | 0.15 | 0.15 | 0.15 | 0.15 | 0.15 | 0.15 | 0.15 |
| O | | Myristyl myristate | 2 | 2 | 2 | 2 | 2 | 2 | 2 |
| O | | Microcrystalline wax | 1 | 1 | 1 | 1 | 1 | 1 | 1 |
| O | | Dimeticone | 3 | 3 | 3 | 3 | 3 | 3 | 2 |
| O | | Squalane | 5 | 4.9 | 4 | 3 | 3 | — | — |
| W | | Triethanolamine | 1.2 | 1.2 | 1.2 | 1.2 | 1.2 | 1.2 | 1.2 |
| P | | Titanium oxide | 1 | 1 | 1 | 1 | 1 | 1 | 1 |
| P | | Spherical cellulose | 0.5 | 0.5 | 0.5 | 0.5 | 0.5 | 0.5 | 0.5 |
| W | | Edetate | 0.1 | 0.1 | 0.1 | 0.1 | 0.1 | 0.1 | 0.1 |
| W | | Phenoxy ethanol | 0.5 | 0.5 | 0.5 | 0.5 | 0.5 | 0.5 | 0.5 |
| W | | Sodiun pyrosulfite | 0.003 | 0.003 | 0.003 | 0.003 | 0.003 | 0.003 | 0.003 |
| W | | Hexametaphosphoric soda | 0.1 | 0.1 | 0.1 | 0.1 | 0.1 | 0.1 | 0.1 |
| P | | Iron oxide (red) | 0.0003 | 0.0003 | 0.0003 | 0.0003 | 0.0003 | 0.0003 | 0.0003 |
| P | | Iron oxide (yellow) | 0.006 | 0.006 | 0.006 | 0.006 | 0.006 | 0.006 | 0.006 |
| W | | Water | Balance | Balance | Balance | Balance | Balance | Balance | Balance |
| | | High temperature stability | ○ | ○ | ○ | ○ | ○ | ○ | Δ |
| | | pH | 7.4 | 7.4 | 7.4 | 7.4 | 7.4 | 7.4 | 7.4 |
| | | Emulsified particle size | ○ | ○ | ○ | ○ | ○ | ○ | ○ |
| | | Cycling stability | ○ | ○ | ◎ | ◎ | ◎ | ◎ | ◎ |
| | | Sensation during use (stickiness) | ○ | ○ | ○ | ○ | ○ | ○ | ○ |
| | | Sensation during use (absorption) | ○ | ○ | ○ | ◎ | ◎ | ◎ | ◎ |

Table 3-1 shows the results of checking condition (F) in claim 3.

The effect of the amount of ingredient F being small is the same as that in Example 1. That is, no increase in the cycling stability or the sensation during use is achieved (Comparative example 3-1).

When there is a certain amount of ingredient F, the cycling stability and the sensation during use improve even more than Example 1 (Examples 14-17).

On the other hand, when the amount of ingredient F is too much, the high temperature stability deteriorates slightly (Comparative example 3-2).

Example 1, Examples 18-21, and Comparative examples 3-3 to 3-4

TABLE 3-2

| | | | Conditions of claim 4 | | | | | | |
|---|---|---|---|---|---|---|---|---|---|
| Part | Ingredient | | Example 1 | Comparative example 3-3 | Example 18 | Example 19 | Example 20 | Example 21 | Comparative example 3-4 |
| O | A-1 | PEG40 stearate | 1.1 | 1.1 | 1.1 | 1.1 | 1.1 | 1.1 | 1.1 |
| O | A-2 | Sorbitan tristearate | 1 | 1 | 1 | 1 | 1 | 1 | 1 |
| O | A-3 | Self emulsified glyceryl stearate | 2.5 | 2.5 | 2.5 | 2.5 | 2.5 | 2.5 | 2.5 |
| O | B | Tert-butylmethoxybenzoylmethane | 2 | 2 | 2 | 2 | 2 | 2 | 2 |
| O | | Bis ethylhexyloxyphenol methoxyphenyl triazine | 0.5 | 0.5 | 0.5 | 0.5 | 0.5 | 0.5 | 0.5 |
| O | C | Octocrylene | 5 | 5 | 5 | 5 | 5 | 5 | 5 |
| O | | Ethylhexyl methoxycinnamate | — | — | — | — | — | — | — |
| W | D | Phenylbenzimidazolesulfonic acid | 2 | 2 | 2 | 2 | 2 | 2 | 2 |
| O | E | Stearyl alcohol | 0.5 | 0.5 | 0.5 | 0.5 | 0.5 | 0.5 | 0.5 |
| O | | Behenyl alcohol | 2 | 2 | 2 | 2 | 2 | 2 | 2 |
| O | | Cetanol | — | — | — | — | — | — | — |
| O | F | 2-ethylhexyl 2-ethylhexanoate | — | — | — | — | — | — | — |
| O | | Isononyl isononanoate | — | — | — | — | — | — | — |
| W | G | PEG/PPG-14/7 dimethyl ether | — | 0.1 | 1 | 2 | — | 5 | 10 |
| W | | PEG/PPG-17/4 dimethyl ether | — | — | — | — | 2 | — | — |
| W | H | Carnosine | — | — | — | — | — | — | — |
| W | Other | Glycerin | 7 | 7 | 7 | 7 | 7 | 7 | 7 |
| W | | Dipropylene glycol | 5 | 5 | 5 | 5 | 5 | 5 | 5 |
| W | | Butylene glycol | 8 | 8 | 8 | 8 | 8 | 8 | 8 |
| W | | Xanthan gum | 0.15 | 0.15 | 0.15 | 0.15 | 0.15 | 0.15 | 0.15 |
| O | | Myristyl myristate | 2 | 2 | 2 | 2 | 2 | 2 | 2 |
| O | | Microcrystalline wax | 1 | 1 | 1 | 1 | 1 | 1 | 1 |
| O | | Dimeticone | 3 | 3 | 3 | 3 | 3 | 3 | 3 |
| O | | Squalane | 5 | 5 | 5 | 5 | 5 | 5 | 5 |
| W | | Triethanolamine | 1.2 | 1.2 | 1.2 | 1.2 | 1.2 | 1.2 | 1.2 |
| P | | Titanium oxide | 1 | 1 | 1 | 1 | 1 | 1 | 1 |
| P | | Spherical cellulose | 0.5 | 0.5 | 0.5 | 0.5 | 0.5 | 0.5 | 0.5 |
| W | | Edetate | 0.1 | 0.1 | 0.1 | 0.1 | 0.1 | 0.1 | 0.1 |
| W | | Phenoxy ethanol | 0.5 | 0.5 | 0.5 | 0.5 | 0.5 | 0.5 | 0.5 |
| W | | Sodium pyrosulfite | 0.003 | 0.003 | 0.003 | 0.003 | 0.003 | 0.003 | 0.003 |
| W | | Hexametaphosphoric soda | 0.1 | 0.1 | 0.1 | 0.1 | 0.1 | 0.1 | 0.1 |
| P | | Iron oxide (red): | 0.0003 | 0.0003 | 0.0003 | 0.0003 | 0.0003 | 0.0003 | 0.0003 |
| P | | Iron oxide (yellow): | 0.006 | 0.006 | 0.006 | 0.006 | 0.006 | 0.006 | 0.006 |
| W | | Water | Balance | Balance | Balance | Balance | Balance | Balance | Balance |
| | | High temperature stability | ○ | ○ | ○ | ◎ | ◎ | ○ | Δ |
| | | pH | 7.4 | 7.4 | 7.4 | 7.4 | 7.4 | 7.4 | 7.4 |
| | | Emulsified particle size | ○ | ○ | ◎ | ◎ | ◎ | ◎ | ◎ |
| | | Cycling stability | ○ | ○ | ○ | ○ | ○ | ○ | ○ |
| | | Sensation during use (stickiness) | ○ | ○ | ○ | ◎ | ◎ | ◎ | ◎ |
| | | Sensation during use (absorption) | ○ | ○ | ○ | ◎ | ◎ | ◎ | ◎ |

Table 3-2 shows the results of checking condition (G) in claim 4.

The effect of the amount of ingredient G being too small is the same as that in Example 1. That is, no increase in the high temperature stability, emulsified particle size or sensation during use is achieved (Comparative example 3-3).

No effect is achieved when the amount of ingredient G is too small (Comparative example 3-3).

When there is a certain amount of ingredient G, the cycling stability and the sensation during use improve (Examples 18-21).

On the other hand, when the amount of ingredient G is too much, the high temperature stability deteriorates slightly (Comparative example 3-4).

Example 1, Examples 22-23, Comparative examples 3-5

TABLE 3-3

| Part | Ingredient | | Example 1 | Example 22 | Example 23 | Comparative example 3-5 |
|---|---|---|---|---|---|---|
| | | | \multicolumn{4}{c}{Conditions of claim 5} |
| O | A-1 | PEG40 stearate | 1.1 | 1.1 | 1.1 | 1.1 |
| O | A-2 | Sorbitan tristearate | 1 | 1 | 1 | 1 |
| O | A-3 | Self emulsified glyceryl stearate | 2.5 | 2.5 | 2.5 | 2.5 |
| O | B | Tert-butylmethoxybenzoylmethane | 2 | 2 | 2 | 2 |
| O | | Bis ethylhexyloxyphenol methoxyphenyl triazine | 0.5 | 0.5 | 0.5 | 0.5 |
| O | C | Octocrylene | 5 | 5 | 5 | 5 |
| O | | Ethylhexyl methoxycinnamate | — | — | — | — |
| W | D | Phenylbenzimidazolesulfonic acid | 2 | 2 | 2 | 2 |
| O | E | Stearyl alcohol | 0.5 | 0.5 | 0.5 | 0.5 |
| O | | Behenyl alcohol | 2 | 2 | 2 | 2 |
| O | | Cetanol | — | — | — | — |
| O | F | 2-ethylhexyl 2-ethylhexanoate | — | — | — | — |
| O | | Isononyl isononanoate | — | — | — | — |
| W | G | PEG/PPG-14/7 dimethyl ether | — | — | — | — |
| W | | PEG/PPG-17/4 dimethyl ether | — | — | — | — |
| W | H | Carnosine | — | 1 | 3 | 4.5 |
| W | Other | Glycerin | 7 | 7 | 7 | 7 |
| W | | Dipropylene glycol | 5 | 5 | 5 | 5 |
| W | | Butylene glycol | 8 | 8 | 8 | 8 |
| W | | Xanthan gum | 0.15 | 0.15 | 0.15 | 0.15 |
| O | | Myristyl myristate | 2 | 2 | 2 | 2 |
| O | | Microcrystalline wax | 1 | 1 | 1 | 1 |
| O | | Dimeticone | 3 | 3 | 3 | 3 |
| O | | Squalane | 5 | 5 | 5 | 5 |
| W | | Triethanolamine | 1.2 | 1.2 | 1.2 | 1.2 |
| P | | Titanium oxide | 1 | 1 | 1 | 1 |
| P | | Spherical cellulose | 0.5 | 0.5 | 0.5 | 0.5 |
| W | | Edetate | 0.1 | 0.1 | 0.1 | 0.1 |
| W | | Phenoxy ethanol | 0.5 | 0.5 | 0.5 | 0.5 |
| W | | Sodium pyrosulfite | 0.003 | 0.003 | 0.003 | 0.003 |
| W | | Hexametaphosphoric soda | 0.1 | 0.1 | 0.1 | 0.1 |
| P | | Iron oxide (red) | 0.0003 | 0.0003 | 0.0003 | 0.0003 |
| P | | Iron oxide (yellow) | 0.006 | 0.006 | 0.006 | 0.006 |
| W | | Water | Balance | Balance | Balance | Balance |
| | | High temperature stability | ○ | ○ | ○ | ○ |
| | | pH | 7.4 | 7.4 | 7.6 | 8.3 |
| | | Emulsified particle size | ○ | ○ | ○ | ○ |
| | | Cycling stability | ○ | ○ | ○ | ○ |
| | | Sensation during use (stickiness) | ○ | ○ | ○ | ○ |
| | | Sensation during use (absorption) | ○ | ○ | ○ | ○ |

Table 3-3 shows the results of checking condition (H) in claim 5.

In the present invention, even when ingredient H is added, the pH is maintained at the same level as in Example 1 (Examples 22 and 23). However, when the amount of ingredient H is too much, the pH exceeds 8 (Comparative example 3-5).

INDUSTRIAL APPLICABILITY

The present invention can provide an oil-in-water emulsified sunscreen cosmetic that is superior in ultraviolet protection as well as in stability and the sensation during use. That is, a sunscreen cosmetic's ultraviolet protection can be increased and also the stability of the base agent and the sensation during use can be improved by providing an oil-in-water emulsified sunscreen cosmetic that satisfies all of the aforementioned conditions (A), (B), (C), (D), and (E).

Also, in the present invention, even when carnosine, which is a prior art antioxidant and anti-wrinkling agent, is added, an increase in the base agent pH due to basic dipeptide carnosine can be prevented. Therefore, a sunscreen cosmetic can stably contain carnosine while maintaining the stability of the base agent and the sensation during use.

The invention claimed is:

1. An oil-in-water emulsified sunscreen cosmetic that satisfies all of the following conditions (A), (B), (C), (D), (E), and (G):
   (A) contains the following three surfactants (A-1)-(A-3) in an amount of 1-6 wt % of the total amount of the cosmetic:
      (A-1) a POE stearic ester having a POE mole number of 20-120,
      (A-2) sorbitan tristearate, and
      (A-3) glyceryl stearate having an HLB of 5-8 which is present in an amount of 10-75 wt % of the total amount of ingredients (A-1), (A-2), and (A-3);
   (B) contains the following oil soluble ultraviolet absorbent, which is solid at room temperature, in an amount of 0.01-5 wt % of the total amount of the cosmetic: bis-ethylhexyloxyphenolmethoxyphenyltriazine and/or tert-butylmethoxybenzoylmethane;
   (C) contains the following oil soluble ultraviolet absorbent, which is liquid at room temperature, in an amount of 1-14 wt % of the total amount of the cosmetic: ethylhexyl methoxycinnamate and/or octocrylene;
   (D) contains the following water soluble ultraviolet absorbent in an amount of 0.1-5 wt % of the total amount of the cosmetic: phenylbenzimidazolesulfonic acid;
   (E) contains higher alcohol having 14-24 carbon atoms which is present in an amount of 30-90 wt % of the total amount of ingredients (A-1), (A-2), and (A-3), and
   (G) contains a random copolymer ether compound of ethylene glycol and propylene glycol represented by the following formula (2) in an amount of 0.2-9 wt % of the total amount of the cosmetic:

RO-[(EO)$_m$(AO)$_n$]—OR  (2)

wherein AO denotes an oxyalkylene group having 3-4 carbon atoms, EO denotes an oxyethylene group, m and n, respectively, are average addition mole numbers of said oxyalkylene group and oxyethylene group; also 1=<m=<70 and 1=<n=<70; the ratio of the oxyethylene group to the total of the oxyalkylene group having 3-4 carbon atoms and the oxyethylene group being 50-100 wt %; the oxyalkylene group having 3-4 carbon atoms and the oxyethylene group being randomly added; R denotes a hydrocarbon group having 1-4 carbon atoms or hydrogen, each different or identical, and the ratio of the number of hydrogen atoms to the number of the hydrocarbon groups is 0.15 or less.

2. An oil-in-water emulsified sunscreen cosmetic that satisfies all of the following conditions (A), (B), (C), (D), (E), and (H):
   (A) contains the following three surfactants (A-1)-(A-3) in the an amount of 1-6 wt % of the total amount of the cosmetic:
      (A-1) a POE stearic ester having a POE mole number of 20-120,
      (A-2) sorbitan tristearate
      (A-3) glyceryl stearate having a an HLB of 5-8 which is present in an amount of 10-75 wt % of the total amount of ingredients (A-1), (A-2), and (A-3),
   (B) contains the following oil soluble ultraviolet absorbent, which is solid at room temperature, in the an amount of 0.01-5 wt % of the total amount of the cosmetic: bis-ethylhexyloxyphenolmethoxyphenyltriazine and/or tert-butylmethoxybenzoylmethane;
   (C) contains the following oil soluble ultraviolet absorbent, which is liquid at room temperature, in the an amount of 1-14 wt % of the total amount of the cosmetic: ethylhexyl methoxycinnamate and/or octocrylene;
   (D) contains the following water soluble ultraviolet absorbent in an amount of 0.1-5 wt % of the total amount of the cosmetic: phenylbenzimidazolesulfonic phenylbenzimidazolesulfonic acid;
   (E) contains higher alcohol having 14-24 carbon atoms which is present in an amount of 30-90 wt % of the total amount of ingredients (A-1), (A-2), and (A-3), and
   (H) contains β-alanyl-L-histidine and/or its salt in an amount of 0.1-4 wt % of the total amount of the cosmetic, said cosmetic having a pH less than 8.

3. The oil-in-water emulsified sunscreen cosmetic of claim 1, wherein the cosmetic further contains (F) mono-ester oil represented by the following formula (1) in an amount of 0.2-9 wt % of the total amount of the cosmetic:

R$_1$COOR$_2$  (1)

wherein R$_1$ denotes an alkyl group having 5-11 carbon atoms, and R$_2$ denotes an alkyl group having 3-11 carbon atoms.

4. The oil-in-water emulsified sunscreen cosmetic of claim 2, wherein the cosmetic further contains (F) mono-ester oil represented by the following formula (1) in an amount of 0.2-9 wt % of the total amount of the cosmetic:

R$_1$COOR$_2$  (1)

wherein R$_1$ denotes an alkyl group having 5-11 carbon atoms, and R$_2$ denotes an alkyl group having 3-11 carbon atoms.

* * * * *